(12) United States Patent
Fesmire et al.

(10) Patent No.: US 6,715,914 B1
(45) Date of Patent: Apr. 6, 2004

(54) APPARATUS AND METHOD FOR THERMAL PERFORMANCE TESTING OF PIPELINES AND PIPING SYSTEMS

(75) Inventors: James E. Fesmire, Titusville, FL (US); Zoltan F. Nagy, Titusville, FL (US); Stanislaw D. Augustynowicz, Titusville, FL (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 0 days.

(21) Appl. No.: 10/185,378

(22) Filed: Jun. 26, 2002

(51) Int. Cl.⁷ .................... G01N 25/00; G01N 17/00; G01K 1/16; G01K 13/02
(52) U.S. Cl. .................... 374/45; 374/57; 374/147
(58) Field of Search .................... 374/45, 57, 54, 374/136, 148, 147, 208

(56) References Cited

U.S. PATENT DOCUMENTS

| | | | |
|---|---|---|---|
| 225,884 A | | 10/1880 | Osborne |
| 3,167,957 A | | 2/1965 | Ziviani |
| 3,453,865 A | | 7/1969 | Blanchard |
| 3,494,145 A | * | 2/1970 | Davis et al. |
| 3,691,840 A | | 9/1972 | Dufour |
| 3,696,677 A | * | 10/1972 | Luedeman |
| 4,036,051 A | | 7/1977 | Fell |
| 4,085,613 A | | 4/1978 | Richard |
| 4,293,916 A | * | 10/1981 | Del Re et al. |
| 4,336,708 A | | 6/1982 | Hobgood |
| 4,396,300 A | | 8/1983 | Characklis |
| 4,469,123 A | * | 9/1984 | Merrill |
| 4,834,550 A | * | 5/1989 | Yano et al. |
| 4,995,731 A | * | 2/1991 | Hori et al. |
| 5,067,094 A | * | 11/1991 | Hayes |
| 5,171,518 A | * | 12/1992 | Barshay et al. |
| 5,308,162 A | * | 5/1994 | Amano et al. |
| 5,659,142 A | | 8/1997 | Lima |
| 5,836,693 A | * | 11/1998 | Stulen et al. |
| 5,980,102 A | | 11/1999 | Stulen |
| 6,047,541 A | * | 4/2000 | Hampton |
| 6,209,350 B1 | * | 4/2001 | Kimble, III |
| 6,257,282 B1 | | 7/2001 | Emmer |
| 6,487,866 B1 | * | 12/2002 | Fesmire et al. |

FOREIGN PATENT DOCUMENTS

GB 1405424 * 9/1975

* cited by examiner

Primary Examiner—Gail Verbitsky
(74) Attorney, Agent, or Firm—Randall M. Heald; Gary G. Borda; John G. Mannix

(57) ABSTRACT

A test apparatus and method of its use for evaluating various performance aspects of a piping segment locates a piping segment between two cold boxes. A first cold box conditions test fluid before providing the fluid into the piping segment. The first and second cold boxes both significantly reduce, if not eliminate, any heat transfer from the ends of the piping so that accurate measurements of heat leak rates from the sides of the piping segment may be determined.

18 Claims, 3 Drawing Sheets

APPARATUS AND METHOD FOR THERMAL PERFORMANCE TESTING OF PIPELINES AND PIPING SYSTEMS

ORIGIN OF THE INVENTION

This invention was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or thereof In accordance with 35 U.S.C. §202, the contractor elected not to retain title.

BACKGROUND OF THE INVENTION

1. Field of the Invention

This invention relates to a mobile test apparatus and a method of making precise thermal performance measurements of process piping and systems, and more specifically to a testing method and apparatus for evaluating thermal insulation systems of pipelines of various media at various temperatures.

2. Prior Art

U.S. Pat. No. 4,978,229 is directed to a method and apparatus for testing thermal conductivity of insulation placed over a test apparatus. While this device is an improvement over the prior art in recognizing that the shape of the insulation contributes to the conductivity of the insulation, this device is not designed, or even capable, of measuring the conductivity of a piping system which is transporting fluid during the test.

U.S. Pat. No. 4,396,300 is directed to a test apparatus for testing the heat transfer and friction characteristics of a tube. It appears that the disclosed apparatus is designed to test an uninsulated tube which would be evaluated for possible use as a heat exchanger tube. There is no provision for eliminating end effects discussed in this reference since the piping segment is a continuous loop. Furthermore, there is no provision for a static boil off test for cryogenic fluids, only a flow through test.

Precise measurement of thermal performance of piping systems is advantageous in certain applications. As technology advances, the use of cryogenics will be more and more commonplace. As an example, hydrogen may provide a more common fuel source. Liquification of hydrogen would then be appropriate for storage in many applications. When handling liquefied gas, i.e., which is typically done at very cold temperatures, there is often a need for cryogenic piping systems.

In the past, data has been obtained from tests of specific segments of a system such as a segment of insulation for a pipe as described in U.S. Pat. No. 4,978,229. The data was then extrapolated as segments were conceptually combined together to approximate the thermal performance of piping systems. Tables provided by certain manufacturers including Chart-CVI of Columbus, Ohio, Chart-MVE, and PHPK include an estimated heat leak rate of some components utilized in the cryogenic piping systems. However, as components are combined together, different components are utilized together, and an approximation, or extrapolation, has been employed to provide an expected thermal performance criteria for the system. However, in field installations, the actual performance values for the insulation system can be as much as 10 to 100 times worse than the ideal laboratory values. Accordingly, a need exists to more definitively predict the thermal performance of actual pipelines and piping systems.

Heat leak measurements for higher performance insulation systems are by nature difficult since small heat leak errors can be very large with respect to the desired measurement. Variables such as external ambient conditions like wind, temperature, humidity, solar radiation, etc. could contribute large errors. Accordingly, a need exists to evaluate a piping configuration with test equipment which can be easily reproduced and provide a standard.

SUMMARY OF THE INVENTION

Consequently, it is a primary object of the present invention to provide a method and apparatus for obtaining data to measure the heat leak rate of cryogenic pipelines.

It is a further object of the present invention to provide a method and apparatus for comparing the thermal performance of piping systems.

Another object of the present invention is to provide a method and apparatus which is easily employed to provide the thermal performance of actual full-scale pipelines and piping systems.

Accordingly, the present invention provides a test apparatus and method to measure the heat leak rate of piping systems. Cold boxes are connected to each end of the piping systems. The test apparatus may be employed in one of two ways: a boil-off method for pipelines carrying cryogenic fluid, or a flow-through evaluation. For the boil off method, the flow rate of boil off is determined for the system, and the heat leak rate may be calculated as the boil-off flow rate times the latent heat of vaporization. For the flow through method, heat leak rate is equal to the liquid mass flow rate times the specific heat and the change in temperature across the system.

The piping system is preferably shrouded with a heater shroud to practically eliminate any environmental effects. Bellows at either end of the piping system allow for thermal expansion and contraction while being equipped to eliminate heat transfer from the pipe ends. Low conductivity pipe supports minimize thermal contact to reduce possible sources of errors. A plurality of temperature and pressure measurement sensors monitor temperatures and pressures at a number of locations to determine the pressures and temperatures at a number of locations along a piping system. Flow meters are also utilized at various locations to evaluate mass flow rates through the piping system. These temperatures, pressures and mass flow rates are utilized to provide the thermal performance characteristics of the piping system.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
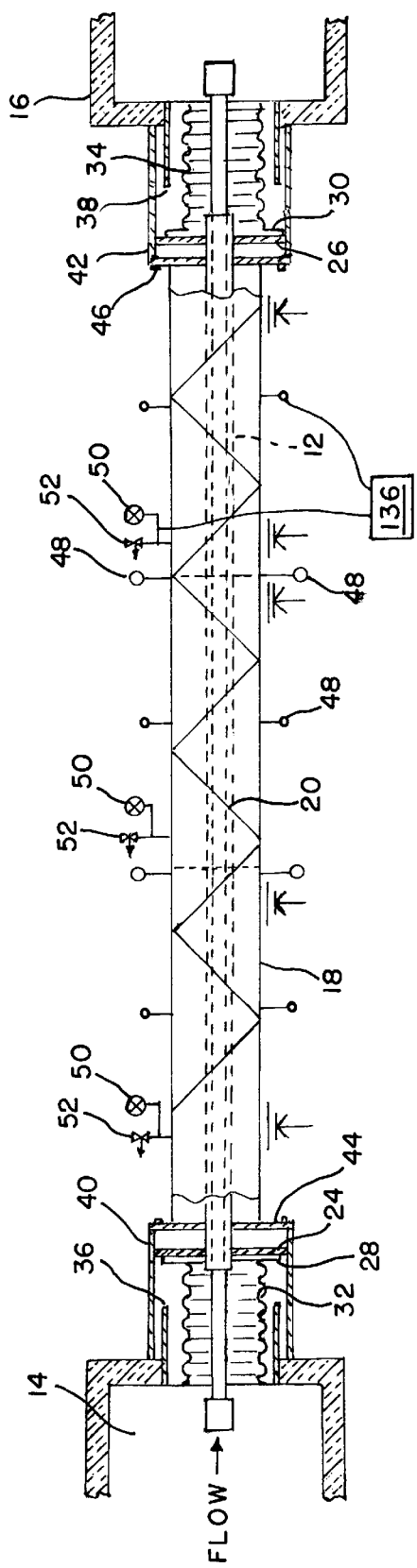
FIG. 1 is a first schematic of a test apparatus illustrating a preferred embodiment of the present invention.

Referring to the FIG. 1, a test apparatus 10 is illustrated. The test apparatus 10 is provided to test the thermal performance of a piping segment 12 so that when the piping segment is utilized in a design, the designers and/or builders may accurately predict the heat losses from the piping segment 12.

Piping segments 12 may include pipe sections, insulation, valves, and/or other components in a stretch of piping which are desired to be evaluated for their thermal performance characteristics such as the heat transfer rate (Q) from a piping segment 12, the Heat Flux rate (q), the apparent thermal conductivity value (k), and the insulating effectiveness value (R). Although a linear piping segment 12 is illustrated, bends and irregularities could be handled as well.

In order to evaluate piping segments 12 under similar conditions so that one piping segment may be compared to another under similar conditions, a test apparatus 10 is useful. The preferred embodiment of the test apparatus 10 has an upstream cold box 14 and a downstream cold box 16. The upstream cold box 14 is useful in conditioning a supply of fluid to be provided into the piping segment 12. Both the upstream and downstream cold boxes 14, 16 are useful in obtaining stability of the piping system, and in eliminating end effects, i.e., errors caused by heat transfer from the pipe ends instead of radially (axially) outwardly from the piping segments 12.

The piping segment 12 is preferably encased within a jacket 18 which is surrounded with a heater 20, illustrated as a heater wire. The heater wire utilized in the preferred embodiment is a 150 W/ft, but other heater designs could be utilized. Within the jacket 18 may be insulation 22 such as Aerogel (TM), MLI, foam, etc. The jacket 18 and heater 20 arrangement has been found helpful in eliminating variable external ambient conditions like wind, temperature, humidity, solar radiation, etc. which could otherwise introduce large errors. In other embodiments, the piping system 12 may be located indoors in a controlled environment rather than outdoors where the preferred embodiment was constructed and has been successfully utilized. In a controlled environment, the heater 20 and jacket 18 could possibly be omitted.

At the ends of the piping segment 12 are inner flanges 24,26 which may be welded, or otherwise connected to the piping segment 12. Outer flanges 28,30 are connected to bellows 32,34 which allow for thermal expansion and contraction of the piping segment 12. Shrouds 36,38 are connected to cold boxes 14,16. External to the shrouds 36,38 are purge cans 40,42 which are filled with insulation, such as aerogel beads or other suitable material. The purge cans 40,42 may be secured with hose clamps, or otherwise. The cans 40,42 have caps 44,46 which may assist in retaining the insulation or temperature boundary within the purge cans 40,42.

The outer flanges 28,30 allow the piping segment 12 to pass through while providing a controlled environment external to the piping segment 12. The controlled environment may be maintained essentially at least up to the inner flanges 28,30, if not all of the way up to the caps 40,42. At various locations along the piping segment, temperature sensors 48, illustrated as thermocouples are placed. The thermocouples may be placed on external surfaces of the piping segment 12, or if internal portions are accessible, such as between pipe portions and insulation, or even within the pipe itself, some sensors may be placed there as well.

Pressure sensors 50, illustrated as pressure transducers, may be utilized if internal portions of the piping segment 12 are accessible to assist in measuring pressure drops of cold vacuum pressure of the piping segment 12. Pressure sensors 50 may also be utilized to monitor pressures within the flow of liquid or for other purposes. A vacuum valve 52 may accompany the pressure sensors 50.

Figure 2:
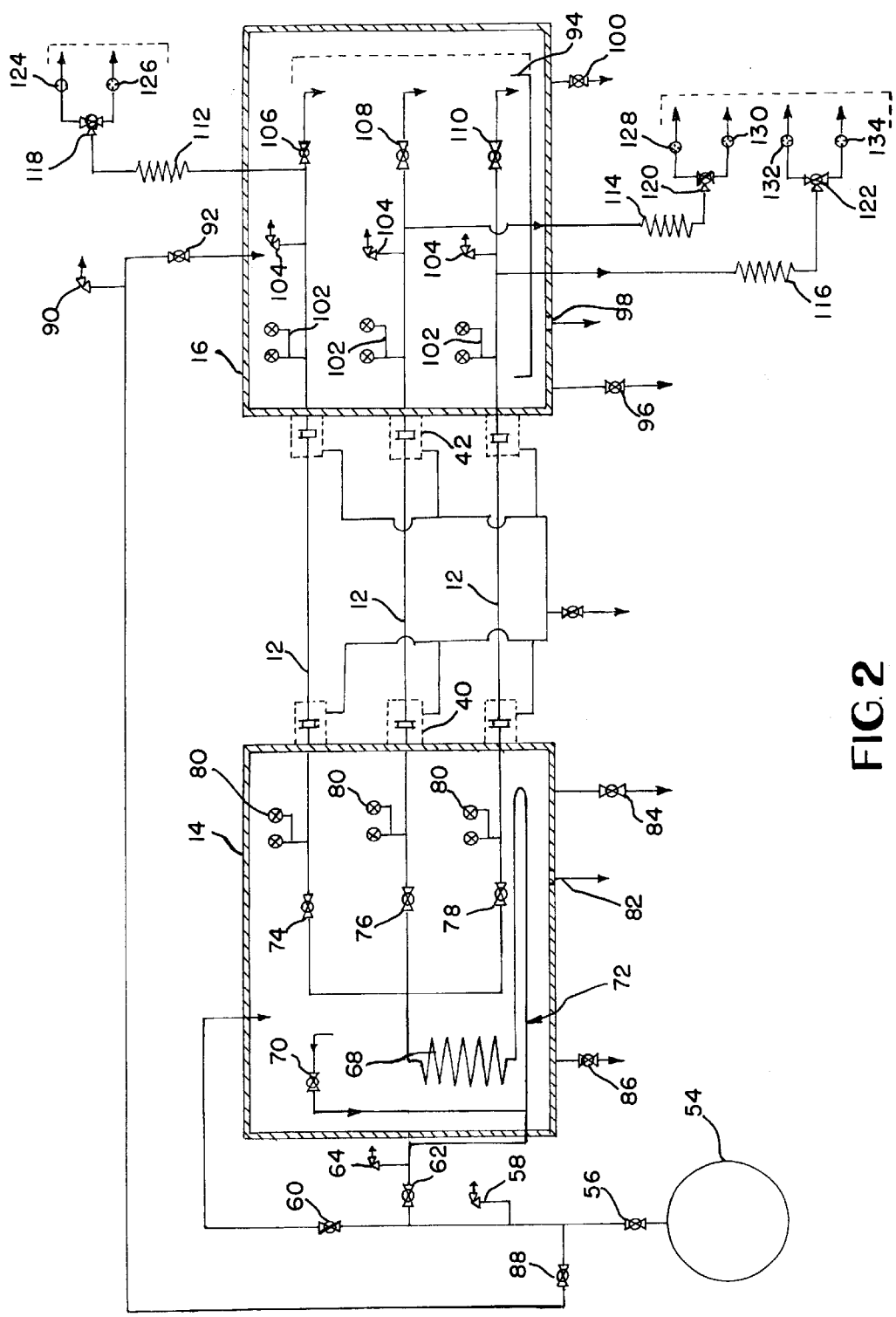
FIG. 2 is a second schematic of the test apparatus showing detail within the cold boxes shown in FIG. 1.

FIG. 2 is helpful in understanding the construction of the cold boxes 14,16 and the piping which supports them when utilized for cryogenic testing. A liquid supply 54 provides liquid nitrogen (LN2), or other appropriate fluid, such as oxygen, or chilled water, etc . . . through cutoff valve 56 to both the cold boxes 14,16. Just past the cutoff valve 56 is a relief valve 58 for safety. The relief valve 58 in the preferred embodiment is set at about forty-five psig. The cold box 14, or upstream box is where the liquid begins and flows to the dowstream box, or cold box 16 through the piping segment 12. In FIG. 2, there are three piping segments 12 illustrated which may be tested simultaneously to reduce costs of conducting the tests.

The upstream box 14 has a box fill valve 60 and a test article fill valve 62. A low pressure relief valve 64 is illustrated downstream of the test article fill valve 62. The fluid from the box fill valve 60 is directed to the box 14 which is utilized to maintain a bath of fluid therein. The bath is utilized as a heat exchanger to cool fluid entering the piping segments 12. The box 14 is open to atmospheric pressure so that the surface temperature of the liquid will be at saturated conditions and thus at the lowest temperature. This colder temperature fluid is utilized to cool the fluid from the supply tank 54 entering the piping segments 12 through coil 68 which is immersed in the bath. A gaseous nitrogen valve 70 may be utilized to precondition the test article if necessary.

The heat exchanger 72 which cools the fluid entering the piping segments 12 is located within the cold box 14. The fluid then passes through an appropriate inlet valve 74,76,78 and past a pressure sensor 80 and into the piping segment(s) 12. The cold box 14 is vented to atmosphere at vent 82. A liquid level control valve 84 allows for liquid to be drained from the box 14. A bottom drain valve 86 is also preferably included on the box 14.

While cryogenic fluid, such as a liquid nitrogen (LN2), is the fluid utilized in a preferred embodiment, chilled water, or other fluids may also be tested with embodiments of the apparatus described herein. A fluid with a normal boiling point below ambient temperature may be used with the apparatus 10.

Before describing the methods of using the apparatus 10, it is helpful to understand the operation of the north cold box 16. Liquid is directed from the supply 54 through a north cold box fill valve 88 past a relief valve 90 and through a fill isolation valve 92 into the downstream box 16. Once again, the fluid is contained in a reservoir 94 to provide a controlled environment to reduce, and hopefully eliminate heat transfer from the ends of the piping segment 12. If the reservoir is overfilled, there is a drain valve 96 which may direct the fluid out of the box 16. Vent 98 is open to atmospheric so that the fluid in the reservoir 94 is at atmospheric pressure. A bottom drain 100 is also preferably installed in the cold box 16.

Inside the downstream cold box 16 are pressure sensors 102 and relief valves 104 for each of the piping segment(s) 12. The low pressure relief valves 104 are set as needed to ensure system safety. Outlet valves 106,108,110 are present as well as conduits to vaporizer coils 112,114,116 located external to the box 16. Downstream of the vaporizer coils 112,114,116 are three way valves 118,120,122 which may be off or direct fluid toward one of two respective flow meters 124,126,128,130,132,134. The relief valves 104 are preferably set at about 50 psig.

Figure 3:
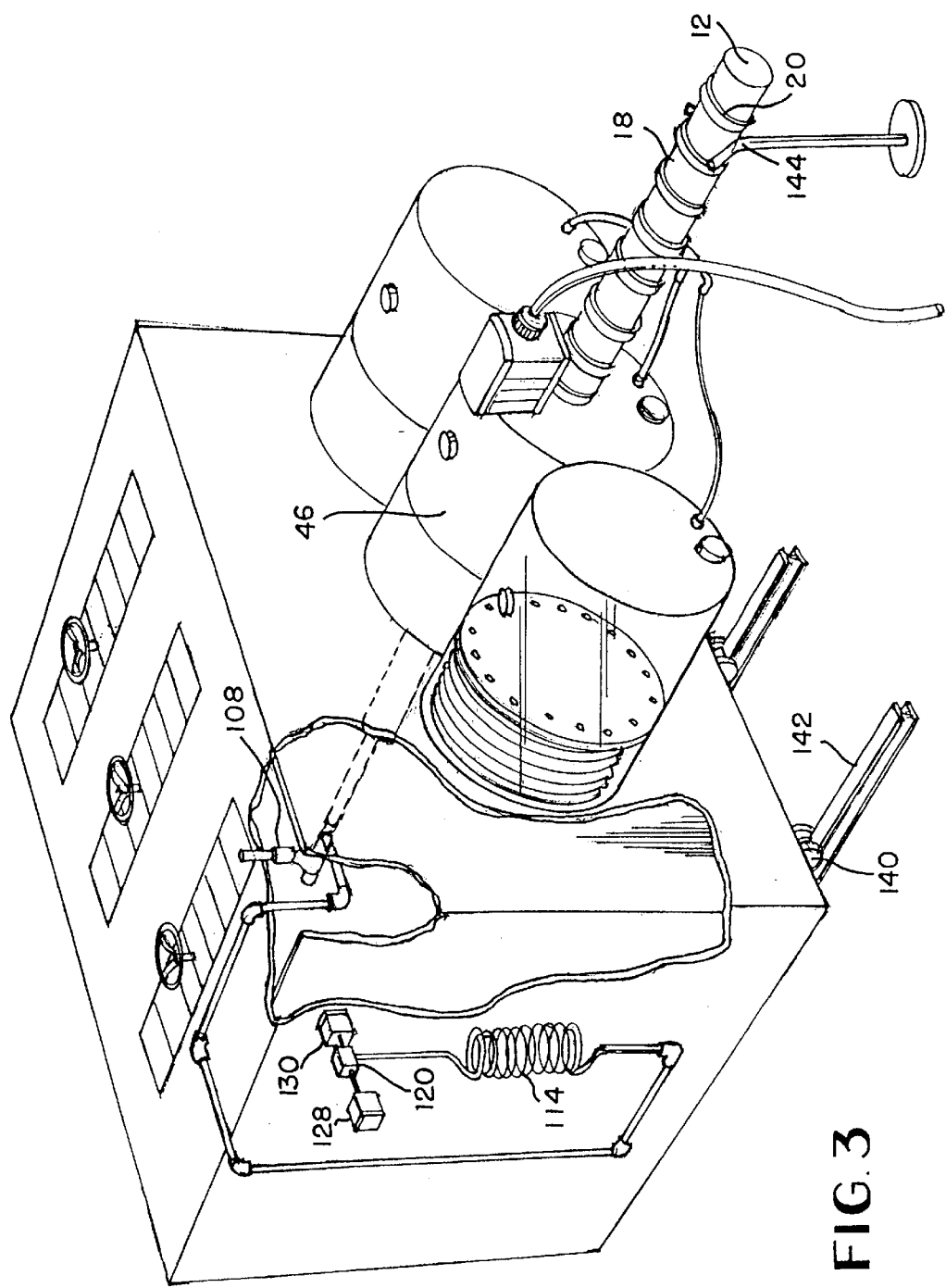
FIG. 3 is a partial cutaway elevational view of one end of the test apparatus of FIG. 1.

Since the cold boxes 14,16 may be similarly constructed, the primary difference in the preferred embodiment being the location of the coils 112,114,116 external to the box 16 instead of within the box as is coil 68 in box 14 for the reasons explained above, only one of the boxes is shown in FIG. 3. Specifically a portion of box 16 is illustrated. The sensors 48,50,80,102 are connected to processor 136 which receives the data and calculates thermal performance parameters of the piping section 12. One or more of the cold boxes 14,16 may have casters 140 which may be constrained by rails 142 to assist in responding to thermal expansion and contraction of the piping section(s) 12. A V-shaped fully adjustable pipe support 144 is illustrated in FIG. 3 supporting the piping system 12. The support 144 has a low conductivity surface indirectly contacting the piping section 12 such as a Teflon (TM) surface.

The test apparatus 10 may be operated for at least two testing procedures. First, a static boil-off test may be performed. When conducting a cryogenic boil off test, the box 14 is filled with liquid at atmospheric pressure. For this example, liquid nitrogen will be the liquid utilized. Accordingly, the temperature of the liquid at atmospheric pressure will be around minus 321 degrees Fahrenheit. Since the pressure in the supply 54 must be somewhat greater than atmospheric pressure so that the fluid will flow. As pressure increases, so does temperature. Accordingly, the temperature in the supply could be as high as minus 302 degrees Fahrenheit, if the liquid were only under about 2 psig of pressure.

Once the bath is established, test fluid is directed through the coil 68 in the heat exchanger 72 which sub-cools the liquid, to near atmospheric saturated temperature. A control flow of liquid as required for a specific test article of steady state condition is obtained through the piping segment 12. The heater 20 establishes a controlled exterior environment to the piping segment 12. The cold boxes 14,16 provide a controlled environment to eliminate any heat transfer into the piping segment 12 at the ends of the piping segment 12.

As the fluid exits the piping system into the downstream cold box 16, it is retained in reservoir 94 which cools the systems within the cold box 16 in a similar manner as the systems in the cold box 14 are cooled with the tank 66.

After achieving steady state, a static boil off test may be performed. To perform the boil off test, the inlet test valve 76 and outlet test valve 108, assuming a single piping segment 12 as shown in FIG. 3 are shut. The flow selector valve 120 is then set to direct gas to one of the two flow meters 128,130. As the pipe warms up, gas separates from the liquid. The piping segment 12 is preferably angled slightly in a cryogenic boil off test, such as at about 2 degrees or greater, so that the gas is directed into the downstream cold box 16 and through the flow meters 128 or 130 to eliminate the formation of a gas pocket in the test article.

The flow meters provide a flow rate (m) to the processor 136. The processor can utilize this data, along with such data as the heat of vaporization at saturation pressure (h), 198.6 J/g to determine the Heat leak rate (Q) since Q=h×m×(delta T). Heat flux rate may be calculated from the heat leak rate (Q) divided by the Mean Heat Transfer Area which is the outside area of the piping system (the insulation outside area, Ao) less the inside area (the sleeve outside area, Ai) divided by the natural log of Ao/Ai. Also, the flow rate (m) is useful in determining the apparent thermal conductivity (k). k=h×m×LN(Do/Di)/2×3.1416×L×(WBT—CBT) where LN is the natural log, Do is the liquid pipe diameter, Di is the Insulation pipe diameter, L is the cold mass length, WBT is the warm boundary temperature and CBT is the cold boundary temperature. Once the apparent thermal conductivity is calculated, the insulation effectiveness (R) may be determined as it is one divided by the apparent thermal conductivity.

In running tests, the R value changes as the temperatures within the pipe change and with time. Graphs of the k or R values and other effectiveness values, such as temperatures, pressures, heat transfer, etc. may be produced. The test apparatus 10 provides a convenient way to standardized the evaluation of piping segments 12. In actual tests, the predicted values of R were attained.

While the boil off method is particularly attractive for determining R values for piping segments 12 utilized in cryogenic systems, a dynamic flow through test may also be performed for cryogenic as well as other liquids, such as chilled water, oil, food product, liquid solid, etc. To perform a dynamic flow through test, inlet test valve 76 and outlet test valve 108 are maintained open after reaching steady state. The temperature at the inlet and the outlet is measured. The difference in temperature is multiplied by the mass flow rate of the liquid flowing the piping and the specific heat value (h) to provide the heat leak rate (Q). The heat flux, apparent thermal conductivity and R value may be calculated as described above.

While the preferred embodiment relates to use with cryogenic fluids, other fluids, including chilled water, and even high temperature fluids, may also utilize a similar test apparatus 10. When evaluating cryogenic pipelines and piping systems, they are typically insulated with high performance materials and have an insulating effectiveness in the range of R-50 to R-2000. When evaluating the cryogenic temperature range, around minus 321 degrees Fahrenheit to the ambient temperature range, around positive 100 degrees Fahrenheit, having a good estimate for the insulation value may be of critical importance. In the past, critical performance of insulation can be 10 to 100 times worse than for the insulation under ideal conditions.

The preferred test apparatus 10 can test three pipelines 12 at a single time, such as with a standard reference pipe in the middle of two proposed designs. Other embodiments can be constructed which can test any number of pipelines 12. The data from the sensors may be compared to determine the performance of the three systems on a relative as well as a quantitative level. With the sensors shown, the apparatus 10 may also be utilized to perform flow analysis experiments, heat leak, pressure drop, multi-phase flow studies, fluid handling component leak measurement, thermal relief characterization, and bleves testing.

Numerous alternations of the structure herein disclosed will suggest themselves to those skilled in the art. However, it is to be understood that the present disclosure relates to the perferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A fluid test apparatus comprising:
a piping segment;
a first cold box located at a first end of the piping segment;
a second cold box located at a second end of the piping segment;
said first cold box, said piping segment and said second cold box forming a continuous fluid passageway;
said first cold box having a heat exchanger to condition a test fluid provided from a supply prior to providing the test fluid to the piping segment, said first and second cold boxes eliminating heat transfer from the ends of the piping segment.

2. The test apparatus of claim 1 further comprising a plurality of temperature sensors located proximate to the piping segment.

3. The test apparatus of claim 1 wherein the second cold box is moveable relative to the first cold box.

4. The test apparatus of claim 1 wherein the cold boxes are connected to the piping segment at flanges and bellows.

5. The test apparatus of claim 1 having a jacket located about the piping segment.

6. The test apparatus of claim 5 wherein the jacket is equipped with a heater.

7. The test apparatus of claim 1 wherein the heat exchanger has a cryogenic fluid exposed to atmospheric pressure which conditions test fluid provided to the piping segment.

8. The test apparatus of claim 7 wherein interior portions of the cold boxes are maintained at a desired temperature with cryogenic fluid exposed to atmospheric pressure.

9. The test apparatus of claim 1 wherein the first cold box has an inlet test valve and the second cold box has an outlet test valve, and said second cold box connected to a coil and a flow meter external to the cold box.

10. A fluid test apparatus comprising:
- a first cold box connected to a first bellows, said first cold box maintained at a predetermined temperature about a portion of a piping segment extending within the first cold box at least to the first bellows;
- the portion of the piping segment extending into the first cold box through the first bellows to a first end;
- a second cold box connected to a second bellows, said second cold box maintained at a predetermined temperature about a further portion the piping segment extending within the second cold box at least to the second bellows;
- the further portion of the piping segment extending into the second cold box through the second bellows to a second end;
- said first cold box, piping segment and second cold box forming a continuous flow passageway; and
- a plurality of temperature sensors located proximate to the piping segment.

11. The test apparatus of claim 10 wherein at least tow of the plurality of temperature sensors are located in a test fluid located within the piping segment.

12. The test apparatus of claim 10 wherein at lease some of the plurality of temperature sensors are located external to the piping segment and along the piping segment.

13. The test apparatus of claim 10 wherein the first cold box further comprises a tank containing fluid to maintain the first end of the piping segment at the predetermined temperature in the first cold box, and the second cold box further comprises a reservoir containing fluid to maintain the second end of the piping segment at the predetermined temperature in the second cold box.

14. A method of evaluating a piping segment comprising:
(a) connecting a first end of a piping segment to a first cold box;
(b) connecting a second end the piping segment to a second cold box, forming a continuous flow passageway through the first cold box, the piping segment and the second cold box;
(c) providing a test fluid through the continuous flow passageway extending through first cold box, the piping segment and the second cold box;
(d) maintaining the piping segment under predetermined conditions;
(e) and conducting a thermal performance test on the piping segment.

15. The method of claim 14 wherein the thermal performance test is a cryogenic boil off test comprising the steps of securing the flow of the test fluid through the piping segment and directing gas through a flow meter at the second cold box, and utilizing a mass flow rate to assist in determining a heat leak rate from the piping.

16. The method of claim 15 further comprising the step of monitoring a warm boundary temperature and a cold temperature with thermal sensors, and utilizing a difference in said temperatures to assist in determining a heat leak rate from the piping segment.

17. The method of claim 14 wherein the thermal performance test is a cryogenic boil off test comprising the steps of securing the flow of test fluid through the piping segment and directing gas through a flow meter at the second cold box, and utilizing a mass flow rate to determine an insulation effectiveness value.

18. The method of claim 14 wherein the performance test is a dynamic flow through test comprising the steps of monitoring the temperature of incoming and outgoing test fluid from the piping segment, and calculating a heat loss rate based on a difference between the incoming and outgoing test fluid temperatures.

* * * * *